United States Patent [19]

Hoffa et al.

[11] Patent Number: 4,635,467
[45] Date of Patent: Jan. 13, 1987

[54] CALIBRATION CELL FOR THE CALIBRATION OF GASEOUS OR NON-GASEOUS FLUID CONSTITUENT SENSORS

[75] Inventors: Jack L. Hoffa, Brea; Maurice N. Karkar, Costa Mesa, both of Calif.

[73] Assignee: American Hospital Supply Corporation, Evanston, Ill.

[21] Appl. No.: 736,767

[22] Filed: May 22, 1985

[51] Int. Cl.$^4$ ............................................. G01C 25/00
[52] U.S. Cl. ................................... 73/1 G; 73/864.83
[58] Field of Search ............... 73/1 G, 864.81, 864.83, 73/864.84, 38

[56] References Cited

U.S. PATENT DOCUMENTS

| | | | |
|---|---|---|---|
| 1,014,842 | 1/1912 | Muckenfuss | 73/38 |
| 3,157,481 | 11/1964 | Bujan | 55/417 |
| 3,631,654 | 1/1972 | Riely et al. | 55/159 |
| 3,698,238 | 10/1972 | Wall et al. | 73/53 |
| 3,707,455 | 12/1972 | Derr et al. | 204/195 |
| 3,718,568 | 2/1973 | Neuwelt | 204/195 |
| 3,719,576 | 3/1973 | Macur | 204/195 |
| 3,882,026 | 5/1975 | McPhee | 210/446 |
| 3,885,414 | 5/1975 | Reville | 73/1 R |
| 3,973,913 | 8/1976 | Louderback | 23/230 |
| 3,975,727 | 8/1976 | Mader et al. | 340/347 |
| 4,003,707 | 1/1977 | Lubbers et al. | 23/232 |
| 4,109,505 | 8/1978 | Clark et al. | 73/1 R |
| 4,126,575 | 11/1978 | Louderback | 252/408 |
| 4,215,940 | 8/1980 | Lubbers et al. | 356/402 |
| 4,221,567 | 9/1980 | Clark et al. | 23/230 |
| 4,260,950 | 4/1981 | Hadden et al. | 324/438 |
| 4,269,685 | 5/1981 | Parker | 204/195 |
| 4,279,775 | 7/1981 | Louderback et al. | 252/408 |
| 4,280,505 | 7/1981 | Dali et al. | 128/635 |
| 4,290,431 | 9/1981 | Herbert et al. | 128/635 |
| 4,306,877 | 12/1981 | Lubbers | 23/230 |
| 4,340,457 | 7/1982 | Kater | 204/195 |

OTHER PUBLICATIONS

R. F. Andritsch et al., *Anesthesiology*, vol. 55, No. 3 (Sep. 1981) pp. 311–316.
1982 Searle Operation Manual, "The Searle In-Line Oxygen Monitoring System".
Searle Brochure, "The Continuous In-Line Oxygen Monitoring System".
1984 American Bentley Gas-STAT TM.
"Understanding and Using the Gas-STAT TM Monitoring System".

*Primary Examiner*—Jerry W. Myracle
*Attorney, Agent, or Firm*—Bernard, Rothwell & Brown

[57] ABSTRACT

A reference liquid-containing calibration cell for the calibration of a sensor for measuring a gaseous or non-gaseous constituent parameter of a fluid includes a chamber containing the reference liquid. The chamber is sealed to prevent loss of the reference liquid, and provides for communication between the sensor and a reference constituent present in the reference liquid. The chamber includes a gas-inleting port sealed by a first semi-permeable membrane which is permeable to a gaseous fluid constituent but impermeable to the reference liquid and non-gaseous reference constituents present in the reference liquid, the chamber further including a gas vent.

18 Claims, 5 Drawing Figures

CALIBRATION CELL FOR THE CALIBRATION OF GASEOUS OR NON-GASEOUS FLUID CONSTITUENT SENSORS

BACKGROUND OF THE INVENTION

1. Field of the Invention

The present invention relates to a reference liquid-containing calibration cell for the calibration of various sensors which measure a gaseous or non-gaseous constituent parameter of a fluid.

2. Description of the Background Art

The use of various sensors to measure gaseous and non-gaseous constituent parameters of fluids has become common in recent years. Such sensors may include electrodes, optodes and the like, and are often used to measure constituent parameters of fluids such as biochemical fluids (e.g., blood), natural or sewage water, ferments, laboratory fluids, and the like.

Fluid constituent parameters which are frequently measured by such sensors include partial pressure of a gas constituent (e.g., $pO_2$ and $pCO_2$), pH, concentrations of various ions (e.g., sodium, potassium, calcium, chloride and the like), and concentrations of various organic molecules such as sugars (e.g., glucose), hormones and enzymes.

Prior to an accurate measurement of a fluid constituent parameter, often it is necessary to calibrate a sensor, including its associated instrumentation. Calibration techniques generally involve bringing a sensor into communication with a reference (calibration) liquid having a known concentration of the constituent to be measured.

A calibration fluid may be prepared for immediate use, however, such preparation is time-consuming and requires skill and accuracy. Once a calibration fluid is prepared, care must be taken to prevent interaction of the fluid with the surrounding environment which might alter its make-up and result in faulty calibrations. Such alterations in the make-up of a calibration fluid may result from permeation, diffusion, chemical reaction, and the like.

Because of the time and skill involved in the preparation of a reference fluid, and as a result of the problems associated with maintaining a reference fluid in usable condition over time, sensors are frequently calibrated using pre-packaged calibration fluids.

Two examples of packaging arrangements for reference solutions are described in U.S. Pat. No. 4,340,457 to Kater. One package includes a pair of electrodes for use as a potassium ion sensor, mounted in openings along the length of a cylinder containing a reference fluid. The cylinder has plastic caps at each end to seal the package. After calibration of the sensor, the caps are removed from the cylinder, the fluid is drained, and the cylinder may be inserted into an extracorporeal blood loop for measuring the potassium ion concentration of a patient's blood.

Another package described in the Kater patent includes a stoppered vial containing a reference fluid. A pair of electrodes for use as a potassium ion sensor are mounted in a catheter which is inserted through the stopper bringing the electrodes into communication with the fluid in the vial. After calibration of the sensor, the catheter may be removed from the vial and inserted into a blood vessel for measuring the potassium ion concentration of a patient's blood.

Because the packages disclosed in the Kater patent are either tightly capped or stoppered, they are not adaptable to calibration fluids for gaseous constituents. It is not practical to pass a reference gas into the calibration fluid contained in the packages described by Kater. The Kater packages are therefore limited to the calibration of sensors for ions or other fluid constituents present in the packaged reference fluid.

Another sealed package for calibration fluids is disclosed in U.S. Pat. No. 3,885,414 to Reville. The calibration fluid may contain pre-determined concentrations of dissolved reference gases (such as oxygen and carbon dioxide) as well as other reference constituents. The sealed package comprises a rigid hollow vessel of non-permeable material such as glass. At least one end of the vessel terminates at a sealed port. For calibration purposes, one end of the vessel is broken off, and the reference fluid is contacted with a sensor. This package has a disadvantage in that the package must be broken open prior to calibration of the sensor, which might result in fluid loss, contamination of the fluid or other detrimental interaction of the fluid with the environment. Another disadvantage is the possibility of chemical reaction between a gaseous reference constituent (particularly oxygen) and another reference constituent during storage of the sealed package, which could result in inaccurate calibration.

There thus remains a need for reference liquid-containing calibration packages or cells into which a reference constituent may be introduced without breaking open the cell and thus exposing the contents to the environment.

SUMMARY OF THE INVENTION

In accordance with the present invention, a reference liquid-containing calibration cell for the calibration of a sensor for measuring a gaseous or non-gaseous constituent parameter of a fluid comprises a chamber containing a reference liquid. The chamber is sealed to prevent loss of the reference liquid, and the chamber includes means for placing a sensor in communication with a reference constituent present in the reference liquid. Means are provided for inleting gas into the chamber, the gas-inleting means including a semi-permeable membrane which is permeable to a gaseous fluid constituent but impermeable to the reference liquid and any non-gaseous reference constituents present in the reference liquid. Means are also provided for venting gas from the chamber.

DETAILED DESCRIPTION OF THE PREFERRED EMBODIMENT

A calibration cell according to the present invention may be used to calibrate a sensor for measuring a gaseous or non-gaseous constituent parameter of a fluid. The concentration and composition of gaseous constituents of the reference liquid may be changed without physically opening the calibration cell. Risks of microbial or chemical contamination or spillage of the reference liquid are therefore minimized.

Gaseous constituent sensors which may be calibrated using the calibration cell of the invention include sensors for measuring the partial-pressures of such gases as oxygen and carbon dioxide which may be present in a fluid. The calibration cell may also be used to calibrate sensors for measuring pH, concentrations of various ions, such as sodium, potassium, calcium, chloride and the like, and concentrations of various organic molecules, such as sugars (e.g., glucose), hormones and enzymes.

Figure 1:
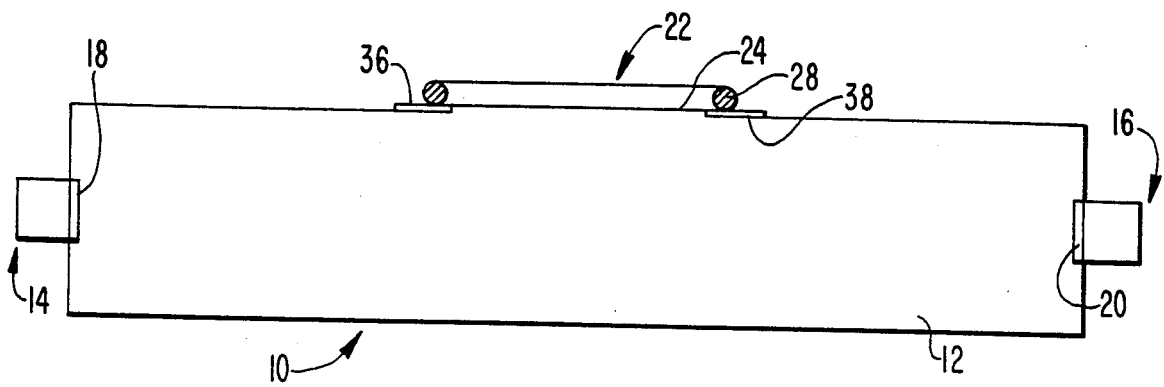
FIG. 1 is a cross-sectional view, partially schematic, of a calibration cell according to the invention.

As shown in FIG. 1, a calibration cell according to the invention includes a chamber 10 for containing a reference liquid 12. Chamber 10 may be of cylindrical shape as shown, or any other suitable shape. Gas inlet port 14 is located at one end of the cylindrical chamber 10, and provides means for inleting a calibration gas into chamber 10. Gas-inleting port 14 is sealed by a semi-permeable membrane 18 which is permeable to a gaseous fluid constituent such as $O_2$ and/or $CO_2$, but impervious to reference liquid 12 and non-gaseous reference constituents present in reference liquid 12, such as ions and/or organic molecules. Membrane 18 prevents biological contamination (e.g., by bacteria) of reference liquid 12 during introduction of gas to the calibration cell.

A means for venting calibration gas from the chamber is also provided. The venting means may include any means through which gas can pass, but does not permit passage of liquid. In the embodiment shown in FIG. 1, the venting means includes a port 16, located at the opposite end of chamber 10 from port 14. In an alternative embodiment, the gas-inleting and gas-venting means is provided by a single port.

According to one embodiment, both ports 14 and 16 are sealed by means of semi-permeable membranes 18 and 20. Each of semi-permeable membranes 18 and 20 is permeable to a gaseous fluid constituent such as $O_2$ and/or $CO_2$, but impervious to reference liquid 12 and non-gaseous reference constituents present in reference liquid 12, such as various ions and/or organic molecules. Semi-permeable membranes 18 and 20 thus allow passage of reference gases into and out of the chamber 10 without allowing the passage of reference liquid 12, or any non-gaseous reference constituents, out of chamber 10.

In an alternative embodiment, gas venting membrane 20 is replaced with an elongated, partially fluid-filled tube, or with a hydrophobic filter as described in U.S. Pat. Nos. 3,631,654 to Reily and 3,157,481 to Bujan. Such hydrophobic filters are commonly used in the medical field to prevent liquid passage while allowing gas to pass therethrough.

A means is provided for placing one or more sensors in communication with reference constituents present in, or introduced into, reference liquid 12. As shown in FIG. 1, this means may include port 22. According to one embodiment, port 22 is sealed by a semi-permeable membrane 24 which is permeable to gaseous and non-gaseous reference fluid constituents, but impervious to reference liquid 12. Membrane 24 is preferably held in place and seals port 22 by means of base member 36 which is connected to chamber 10 by a detachable sealing means 38.

In an alternative embodiment, calibration gas is vented from chamber 10 through port 22 and membrane 24. According to this embodiment, gas-venting port 16 is not required.

In another embodiment, port 22 is replaced by an optionally transparent window, e.g., of transparent plastic or glass, for the calibration of optical sensors.

Figure 4:
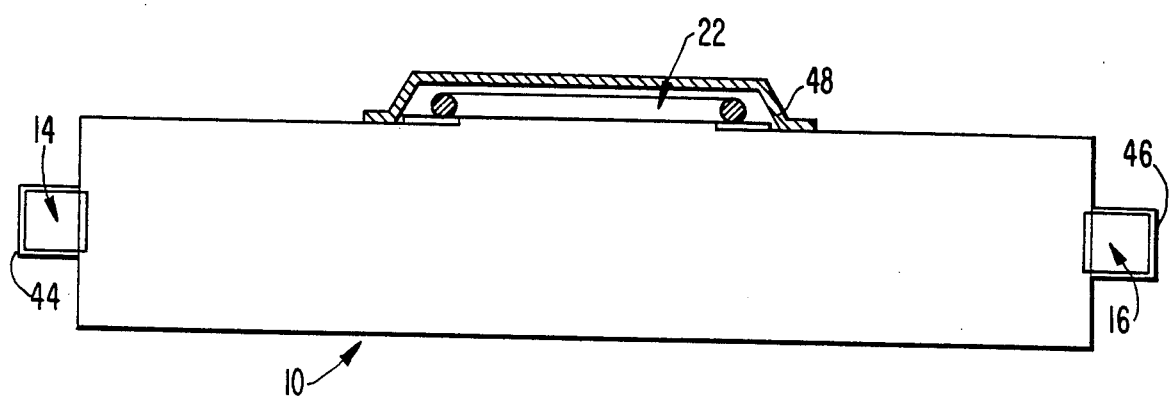
FIG. 4 is a cross-sectional view, partially schematic, of the calibration cell shown in FIG. 1 with removable port caps in place.

The ports are preferably provided with outer removable caps of impermeable material which seal the ports prior to use of the calibration cell. See FIG. 4. The removable caps 44, 46 and 48 seal ports 14, 16 and 22, respectively, prior to use of the calibration cell, and prevent diffusion of materials into or out of reference liquid 12.

Figure 2:
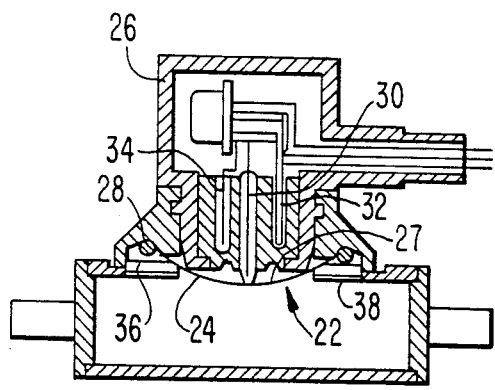
FIG. 2 is a cross-sectional view, partially schematic, of the calibration cell of FIG. 1 connected to a sensor housing containing fluid-constituent sensors.

FIG. 2 illustrates a sensor assembly attached to the calibration cell of FIG. 1. The sensors in the assembly are encased in a housing 26 having an opening 27 to which base member 36 is complementary, thus forming an enclosure for the sensors and membrane 24. Removal of cap 44 (FIG. 4) permits the hook up of a calibration gas line (not shown), removal of cap 48 permits hook up of housing 26 to the calibration cell with accompanying sensors, and removal of cap 46 permits venting of calibration gases from the cell. Sealing means, such as O-ring 28 is provided to tightly seal the connection between housing 26 and base member 36.

According to one embodiment, port 22 is sealed by a semi-permeable membrane 24 which is permeable to gases and hydrogen ions, but impervious to reference liquid 12. With port 14 connected to a source of calibration gases such as $O_2$ and $CO_2$ (not shown), a calibration cell according to this embodiment which contains a buffered reference liquid 12 of, for example, pH 7.4 is suitable for the simultaneous calibration of $pO_2$, $pCO_2$, and pH sensors while passing calibration gases through membrane 18 into reference liquid 12, and venting calibration gas through port 16.

The sensors encased in housing 26 are preferably optical sensors utilizing fluorescent materials which are sensitive to the concentration levels of the constituents being measured. Light of a specific color is transmitted to the fluorescent material of a sensor by means of a fiberoptic cable (not shown). The transmitted light causes molecular excitation of the fluorescent material which, depending upon the concentration of the constituent being measured, emits light of a color different from the transmitted light. The emitted light is transmitted from the sensor by another fiberoptic cable and detected using equipment known in the art. The intensity of the fluorescence can then be correlated with the concentration of the substituent being measured.

With the housing 26 securely connected to calibration chamber 10, hydrogen ions pass through membrane 24 and the pH sensor 30 may be calibrated to the pH of reference liquid 12.

In order to calibrate the $pO_2$ sensor 32 and $pCO_2$ sensor 34, calibration gases ($O_2$ and $CO_2$) are passed from a source (not shown) through the reference liquid 12 by means of a connection (not shown) to port 14, to form a known partial pressure of the reference gases in the reference fluid 12. As the reference gases diffuse across semi-permeable membrane 24, sensors 32 and 34 are calibrated by adjusting their readings to correspond to the known partial pressure of the respective gases in the reference liquid. Calibration gases are vented through port 16 or, e.g., through a vent in housing 26.

Figure 3:
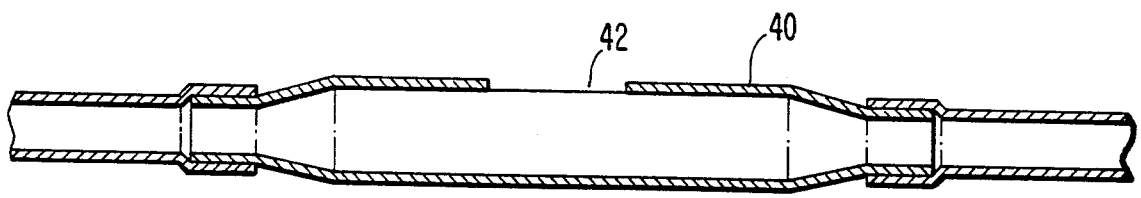
FIG. 3 is a cross-sectional view, partially schematic, of an extracorporeal blood loop fitting for connection with calibrated sensors contained in the sensor housing shown in FIG. 2.

After calibration of sensors 30, 32 and 34, housing 26 along with base member 36 and membrane 24, to which the housing is connected, may be simultaneously detached from chamber 10 by breaking sealing means 38. Membrane 24 may then be contacted with a fluid, such as blood, to measure pH and gas parameters of the fluid. See FIG. 3. Contact between membrane 24 and the blood to be analyzed is advantageously accomplished through an extracorporeal blood loop having a fitting 40 with an opening 42 which mates with and forms a tight seal with the membrane assembly 36. With the sensors calibrated and thus in place in the extracorporeal blood loop, the pH and blood gas parameters of a patient's blood may be monitored continuously.

In another embodiment, the calibration cell is provided with three ports 14, 16 and 22 and membranes 18 and 20 with characteristics as described above. (See FIG. 1.) According to this embodiment, however, membrane 24 comprises a semi-permeable membrane permeable to a gaseous fluid constituent and at least one non-gaseous reference constituent present in the reference liquid 12, but impermeable to the reference liquid 12. A calibration cell according to this embodiment, containing a reference liquid 12 having non-gaseous reference constituents, allows the calibration of corresponding sensors for measuring the parameters of non-gaseous constituents such as ions, including sodium, potassium, calcium, and the like, and organic molecules, such as glucose and various enzymes, as well as pH and gaseous fluid constituents, such as oxygen and carbon dioxide. A calibration cell according to this embodiment is preferably provided with removable caps 44, 46 and 48 as described above with reference to FIG. 4.

In addition to the calibration of one or more sensors such as are contained in housing 26, the removal of base member 36 and membrane 24, permits the attachment of a second type of sensor housing 50 over port 22. (See FIG. 5.) Housing 50 has a base portion 52 corresponding to and mating with port 22, and contains one or more sensors, such as sensor 54, 56 and 60. According to this embodiment, sensors 54 and 56 come in direct contact with reference liquid 12 inside cell 10. Liquid 12 inside cell 10 allows hydration of the sensors before they are used. Sealing member 58, through which probes 54 and 56 extend, is connected to base portion 52 and extends across port 22, thus preventing liquid 12 from passing into housing 50. Sealing member 58 may be constructed of impermeable material, or, alternatively, may comprise a semi-permeable membrane with characteristics similar to membranes 18 and 20 for the calibration of one or more gas sensors 60.

Figure 5:
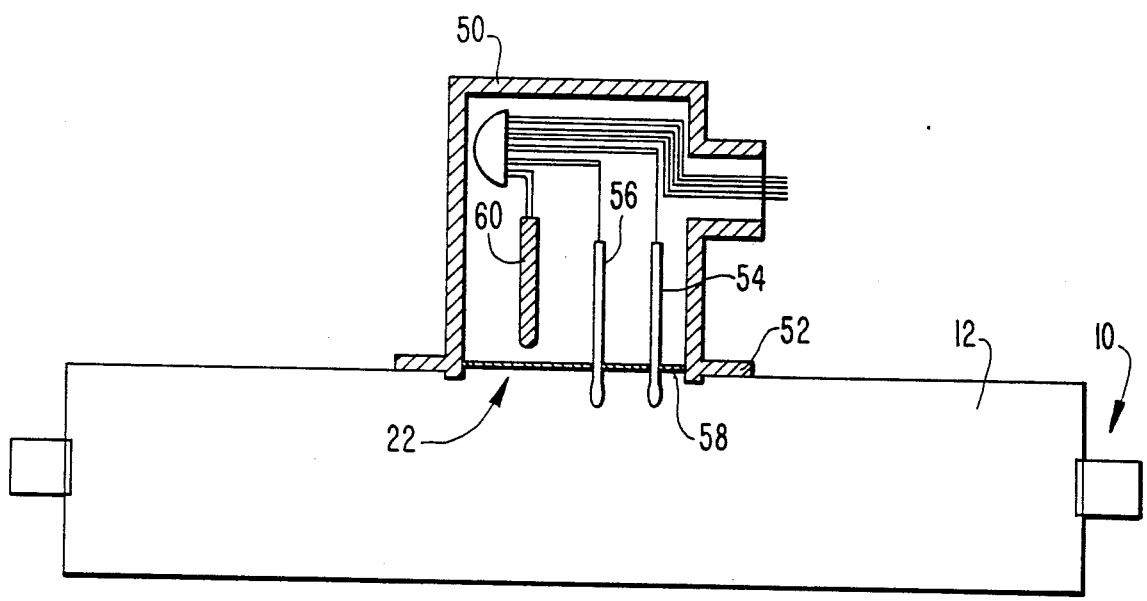
FIG. 5 is a cross-sectional view, partially schematic, of a calibration cell according to another embodiment of the invention.

Alternatively, a calibration cell as shown in FIG. 5, along with housing 50 and accompanying sensors, are provided as a unit with housing 50 being detachably connected to calibration cell 10.

After calibration of the sensors, housing 50 may be detached from calibration cell 10, and connected to an extracorporeal blood loop as described above for measuring fluid constituent parameters.

A calibration cell according to the invention is preferably constructed of an optically opaque material. Optical isolation allows the calibration of optical sensors in addition to sensors of other types.

In yet another embodiment, membranes 18 and 20 are detachably connected to calibration cell 10 by any suitable means. After calibration of one or more sensors contained in a sensor assembly housing connected to the calibration cell, membranes 18 and 20 are detached from the calibration cell 10, and the reference liquid is drained. The calibration cell, along with the attached sensor assembly, can then be directly incorporated into an extracorporeal blood loop by connecting conduits of the loop directly to ports 14 and 16 of calibration cell 10. The constituent parameters of a patient's blood flowing through the loop and the calibration cell may then be monitored continuously.

A calibration cell according to the present invention allows simultaneous or sequential calibration of several sensors for measuring gaseous or non-gaseous constituent parameters of a fluid. Gas parameter sensors may thus be simultaneously calibrated along with pH sensors and other non-gaseous constituent sensors, without the leakage of reference fluid from the calibration cell. Calibrated sensors may thereafter be used to measure constituent parameters of a fluid. For example, the sensor may be used in an extracorporeal blood loop, or for in vivo blood, in vitro analyses of blood, other body fluids, and laboratory fluids.

The sealed ports of the calibration cell prevent leakage of reference fluid from the chamber, and the gas inlet port membrane prevents contamination of the reference fluid by non-sterile gases. Reference gases may be changed or added to reference liquid contained within the calibration cell without the necessity of physically opening the cell, and reference gas or gases may be introduced into the cell immediately prior of sensor calibration, thus reducing the risk of faulty calibration due to reaction between the calibration gases and other reference constituents.

Since many modifications, variations and changes in detail may be made to the described embodiment, it is intended that all matter in the foregoing description and shown in the accompanying drawings be interpreted as illustrative and not in a limiting sense.

What is claimed is:

1. A reference liquid-containing calibration cell for the calibration of a sensor for measuring a gaseous or non-gaseous constituent parameter of a fluid, comprising a chamber containing a reference liquid, wherein said chamber is sealed to prevent loss of said reference liquid, and wherein said chamber includes:
   (a) means for inletting gas into the chamber, the gas-inletting means including a first semi-permeable membrane permeable to a gaseous fluid constituent but impermeable to said reference liquid and non-gaseous reference constituents in the reference liquid;
   (b) means for placing a sensor in communication with a reference constituent present in said reference liquid, said means comprising a port sealed by a second semi-permeable membrane permeable to the gaseous fluid constituent but impermeable to said reference liquid and non-gaseous reference constituents present in the reference liquid; and
   (c) means for venting gas from the chamber.

2. The calibration cell of claim 1 wherein the gas-inleting means comprises a first port sealed by said membrane.

3. The calibration cell of claim 2 wherein said means for placing a sensor in communication with a reference constituent in said reference liquid comprises a second port sealed by a second semi-permeable membrane permeable to a gaseous fluid constituent and a non-gaseous constituent present in said reference liquid, but impermeable to said reference liquid.

4. The calibration cell of claim 3 wherein the venting means comprises a third port sealed by a third semi-permeable membrane permeable to a gaseous fluid constituent but impermeable to said reference liquid and a non-gaseous reference constituent present in the reference liquid.

5. The calibration cell of claim 4 wherein additionally the periphery of the second membrane is attached to and supported by a base member, wherein said base member and second membrane are detachably connected to said chamber by a first sealing means for providing a seal between the base member and the chamber.

6. The calibration cell of claim 5 wherein said calibration cell further comprises a sensor assembly including a sensor housing providing an enclosure for said sensor, and providing means for placing said sensor into communication with a fluid constituent, and wherein said means for placing said sensor into communication with a fluid constituent corresponds to and mates with said base member.

7. The calibration cell of claim 6 wherein said base member further includes a second sealing means for providing a seal between said base member and said housing.

8. The calibration cell of claim 5 further comprising a first outer removable cap of impermeable material sealing said first port, a second outer removable cap of impermeable material sealing said second port, and a third outer removable cap of impermeable material sealing said third port; wherein said first membrane is intermediate between said reference liquid and said second cap, said second membrane is intermediate between said reference liquid and said first cap, and said third membrane is intermediate between said reference liquid and said third cap.

9. The calibration cell of claim 4, wherein said reference liquid is a calibration liquid for pH, $pO_2$, or $pCO_2$, ions selected from the group consisting of sodium, potassium, and chloride, or organic molecules selected from the group consisting of glucose and enzymes, or combinations thereof.

10. The calibration cell of claim 3, wherein said reference liquid is a calibration liquid for pH, $pO_2$, or $pCO_2$, ions selected from the group consisting of sodium, potassium, and chloride, or organic molecules selected from the group consisting of glucose and enzymes or combinations thereof.

11. The calibration cell of claim 1 wherein the venting means comprises a third port sealed by a third semi-permeable membrane permeable to a gaseous fluid constituent but impermeable to said reference liquid and a non-gaseous reference constituent present in the reference liquid.

12. The calibration cell of claim 11 wherein additionally the periphery of the second membrane is attached to and supported by a base member, wherein said base member and second membrane are detachably connected to said chamber by a first sealing means for providing a seal between the base member and the chamber.

13. The calibration cell of claim 12 wherein said calibration cell further comprises a sensor assembly including a sensor housing providing an enclosure for a sensor and providing means for placing said sensor into communication with a fluid constituent, and wherein said means for placing said sensor into communication with a fluid constituent corresponds to and mates with said base member.

14. The calibration cell of claim 13 wherein said base member further includes a second sealing means for providing a seal between said base member and said housing.

15. The calibration cell of claim 12 further comprising a first outer removable cap of impermeable material sealing said first port, a second outer removable cap of impermeable material sealing said second port, and a third outer removable cap of impermeable material sealing said third port; wherein said first membrane is intermediate between said reference liquid and said second cap, said second membrane is intermediate between said reference liquid and said first cap, and said third membrane is intermediate between said reference liquid and said third cap.

16. The calibration cell of claim 11, wherein said reference liquid is a calibration liquid for pH, $pO_2$, or $pCO_2$ or combinations thereof.

17. The calibration cell of claim 1 wherein the means for placing a sensor in communication with a reference constituent comprises a port, the calibration cell further comprising a housing member encasing a sensor, said housing member having an opening around the periphery of which is located a housing base portion which corresponds to and mates with said port, wherein said sensor is in communication with a reference constituent present in said reference liquid, and wherein said housing member is detachably connected to said chamber and seals said port.

18. The calibration cell of claim 1, wherein said reference liquid is a calibration liquid for pH, $pO_2$, or $pCO_2$ or combinations thereof.

* * * * *